United States Patent [19]

Sekine

[11] Patent Number: 4,960,327

[45] Date of Patent: Oct. 2, 1990

[54] OPTICAL SYSTEM IN A LASAR SCANNING EYE FUNDUS CAMERA

[75] Inventor: Ahihiko Sekine, Tokyo, Japan

[73] Assignee: Kabushiki Kaisha Topcon, Tokyo, Japan

[21] Appl. No.: 212,388

[22] Filed: Jun. 27, 1988

[30] Foreign Application Priority Data

Jul. 15, 1987 [JP] Japan .................................. 62-176760
May 9, 1988 [JP] Japan .................................. 63-112070

[51] Int. Cl.$^5$ .............................................. A61B 3/10
[52] U.S. Cl. .................................... 351/221; 351/205; 351/211
[58] Field of Search .............. 351/205, 211, 221, 206; 354/62; 606/4, 5, 6

[56] References Cited

U.S. PATENT DOCUMENTS 4,764,005 8/1988 Webb et al. ......................... 351/205

*Primary Examiner*—Rodney B. Bovernick
*Attorney, Agent, or Firm*—Finnegan, Henderson, Farabow, Garrett & Dunner

[57] ABSTRACT

The present invention relates to the optical system in a laser scanning eye fundus camera. The optical system comprises: an illuminating optical system for scanning an eye fundus with an illuminating laser light beam from a light source using a light scanning device; a light receiving optical system for directing the reflected light from the eye fundus to a light receiver unit; and a beam diameter adjusting means associated with said optical systems for adjusting the beam diameter of the laser beam or of the light for observation. Such arrangement according to the present invention allows to adjust the depth of field by adjusting the aperture diameter of the optical system by means of the beam diameter adjusting means so that test or inspection of even or uniform quality can be ensured for all subject in spite of variations in their age, experience of medical or opthalmological tests or inspections, or structure of the eye fundus.

1 Claim, 7 Drawing Sheets

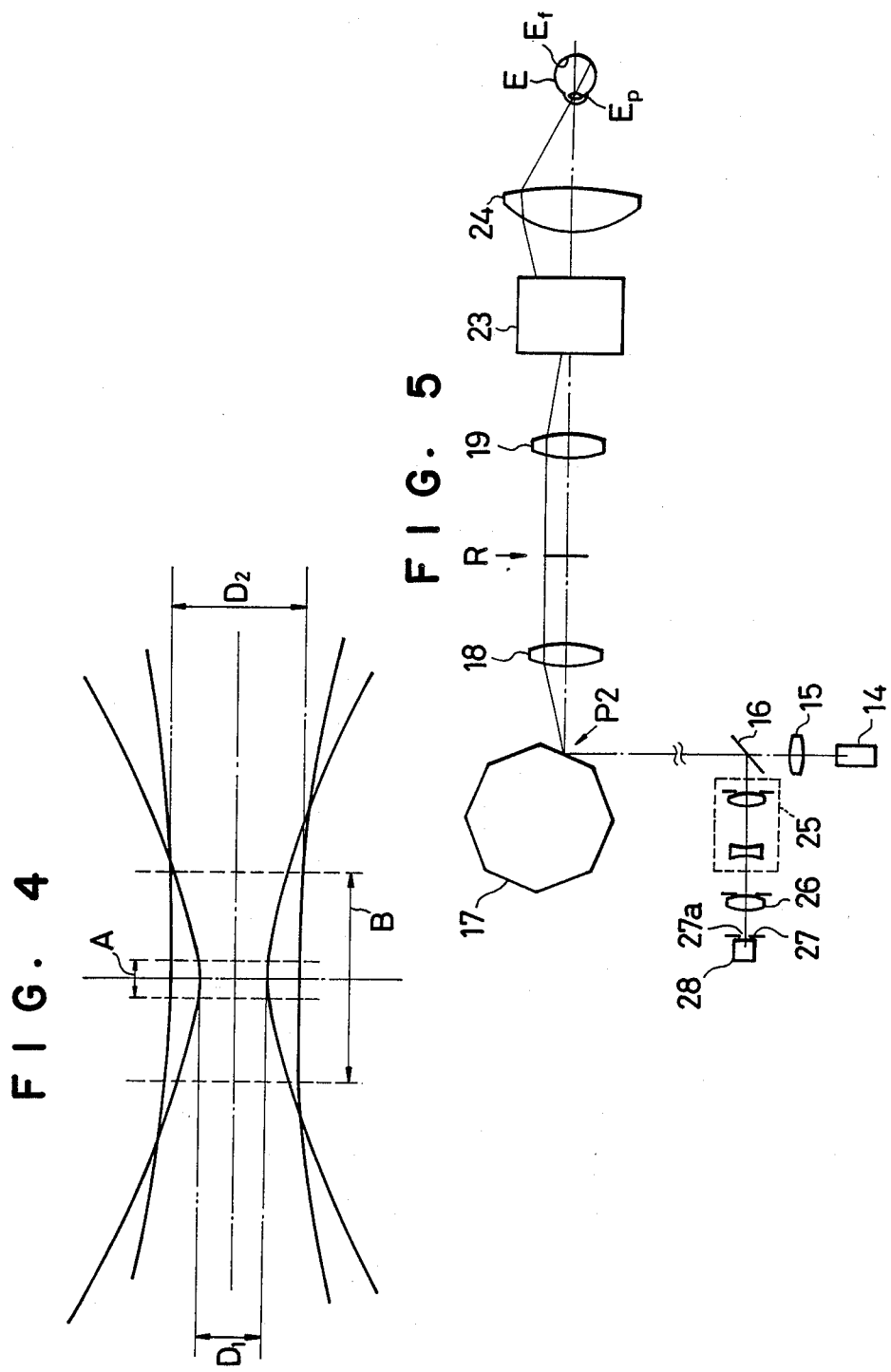

OPTICAL SYSTEM IN A LASAR SCANNING EYE FUNDUS CAMERA

FIELD OF THE INVENTION

The present invention relates to the optical system in a laser scanning eye fundus camera which scans the fundus of a subject's eye with an illuminating laser beam.

BACKGROUNG OF THE INVENTION

Conventional eye fundus cameras are arranged to uniformly illuminate the whole of the subject's eye fundus so as to observe or photograph it. The eye fundus must then be illuminated with a relatively intense flux of light which might regrettably cause pain to the subject.

In recent years, a new type of eye fundus camera has been developed which reduces such pain. It is adapted to scan the subject's eye fundus with an illuminating laser beam having a constant spot diameter and to detect the reflected light from the eye fundus at constant intervals, each interval being equal to the spot diameter of the laser beam. The data derived from the reflection due to spot illumination is used to construct an image of the fundus of the subject's eye on a monitor cathode ray tube (CRT).

Meanwhile, as illustrated in FIG. 4, the depth of focus for such a laser beam becomes shallower (space A) as the spot diameter, or the diameter of the cross section, of the laser light beam and hence the F-number are reduced (indicated by $D_1$). It conversely becomes deeper (space B) as the spot diameter and hence the F-number are increased (indicated by $D_2$).

The eye fundus is not smooth but rugged. To obtain a clear image of the eye fundus, therefore, the depth of focus for the laser beam should be deeper and hence the spot diameter of the laser beam should be larger to some extent.

In prior art apparatuses of the last-mentioned type, however, the laser beam diameter is invariably set to a very small value in order to obtain signals due to spot illumination more than the number of picture elements of the associated monitor CRT. As a result, there is a problem with the prior art apparatus in that the depth of focus is relatively shallow and the image of the subject's eye fundus can become out of focus if the eye slightly moves relative to the apparatus. There is a tendency for young persons, in particular, to move the head or eyes while undergoing the ophthalmological inspection or test. Thus, it is desirable for the apparatus to have means for varying the spot diameter such that a clear image of the eye fundus can be obtained in spite of possible slight movement of the subject's eye relative to the apparatus. It is also desirable for the apparatus to be able to reduce the spot diameter so as to achieve a high resolution.

An eye fundus camera of such type is known in which, for the purpose of achieving a high contrast image, a light beam scanning device is commonly used by both an illuminating optical system for emitting a laser light beam and a light receiving optical system for directing the reflected light or fluorescence from the eye fundus. In this eye fundus camera, a pin hole or diaphragm is provided in the light receiving optical system at a position which is optically conjugate with the eye fundus under test. The diameter of the pin hole determines the diameter of the spot of light projected onto the eye fundus, or the size of each picture element, whereby the resolution is determined.

In other words, the light receiving optical system of the eye fundus camera of the above-described type is designed such that only the light reflected from a particular region of the eye fundus, i.e. the region onto which an image of the pin hole is projected by the light receiving optical system, can pass through the pin hole. Thus, even if the illuminating light spot on the eye fundus is greater than the pin hole image on the eye fundus, the light reflected from outside the region of the pin hole image cannot pass through the pin hole. The resolution of the image of the eye fundus is therefore determined by the pin hole image on the eye fundus. Thus, the resolution of the apparatus of such an arrangement is determined by its optical system which projects the pin hole, i.e. the light receiving optical system.

In order that the eye fundus camera of such type can receive as large an amount of reflected light as possible at its light receiver part from the eye fundus so as to have a high resolution, the diameter of the laser beam from the illuminating optical system should be variable in accordance with the scanning magnification for the subject's eye fundus and further the diameter of the aperture of the light receiving optical system should be as large as possible.

There is however a problem in that, as the aperture diameter of the light receiving optical system is increased, the resolution becomes higher but at the same time the depth of field becomes shallower, with the result that the whole of the eye fundus cannot be in focus at one time and it will be out of focus due to only slight movement of the subject's eye relative to the apparatus.

SUMMARY OF THE INVENTION

The primary object of the present invention is therefore to provide the optical system in a laser scanning eye fundus camera, which is capable of adjusting the depth of field so as to obtain an even or uniform quality of the ophthalmological inspection or test for all subjects in spite of variations between them, in age, experience of ophthalmological inspection or test, or structure of the eye fundus, for example. In other words, the primary object of the present invention is to provide the optical system in a laser scanning eye fundus camera, which is provided with adjusting means for adjusting at least one of the apertures of the illuminating and light-receiving system thereby to adjust the depth of field, whereby an even or uniform quality of the ophthalmological inspection or test can be ensured for all subjects in spite of variations in their age or conditions.

To achieve this object, the optical system in a laser scanning eye fundus camera according to the present invention is provided with an illuminating optical system for scanning an eye fundus with an illuminating laser beam from a light source using a light scanning device, a light receiving optical system for directing the reflected light from the eye fundus to a light receiver unit, and a beam diameter adjusting means associated with said optical system for adjusting the beam diameter of the laser beam or of the light for observation.

Another object of the present invention is to provide the optical system in a laser scanning eye fundus camera, in which the operator can change the spot diameter for a very young subject who is likely to move the eyes during the test or inspection, whereby a clear image of the eye fundus can be obtained in spite of slight movement of the subject's eye. A further object of the present invention is to provide the optical system in a laser scanning eye fundus camera, which is capable of reducing the spot diameter so as to obtain a high resolution.

To achieve this object, and in view of the fact that the diameter of the spot affects the depth of field, the present invention provides the illuminating optical system with spot diameter adjusting means for allowing the operator to adjust the spot diameter as necessary.

A still further object of the present invention is to provide the optical system in a laser scanning eye fundus camera which allows one to obtain a high resolution by means of the light receiving optical system.

To achieve this object, the present invention provides the light receiving optical system with beam diameter adjusting means.

Other objects and features of the invention will readily be understood from the following detailed description and the accompanying drawings.

BRIEF DESCRIPTION OF THE DRAWINGS

FIG. 4 is an illustration showing the relationship between the diameter of the laser beam and the depth of focus.

FIG. 5 is a schematic plan view showing the arrangement of another embodiment of the optical system in the laser scanning eye fundus camera according to the present invention.

DESCRIPTION OF THE PREFERRED EMBODIMENTS

A preferred embodiment of the present invention will now be described with reference to FIGS. 1 through 4.

Figure 1:
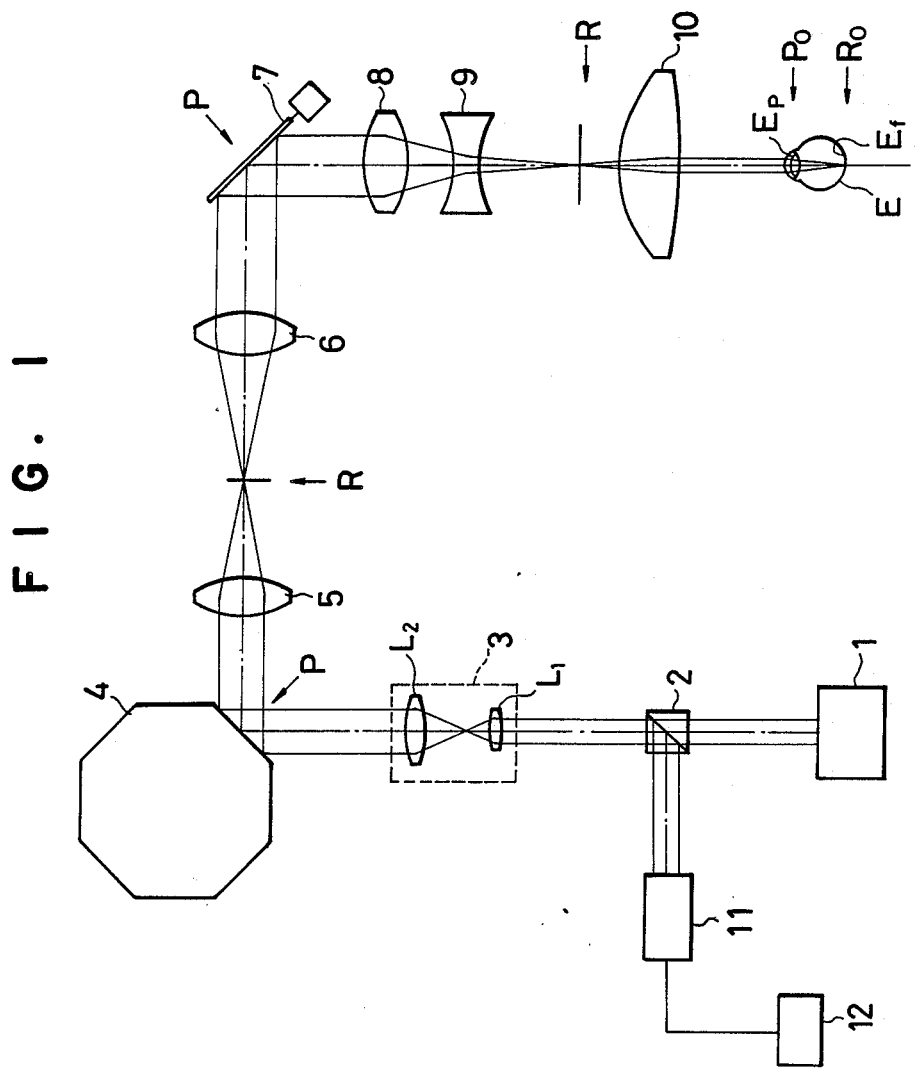
FIG. 1 is an illustration of an embodiment of the optical system in the laser scanning eye fundus camera according to the present invention.
Figure 2:
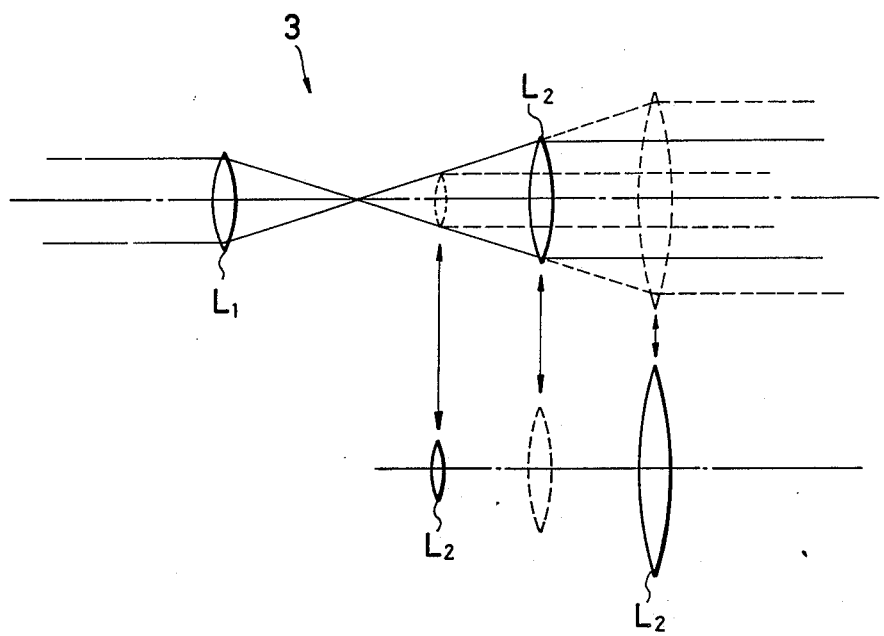
FIG. 2 is an illustration showing an alternative example of the beam expander shown in FIG. 1.

FIG. 1 shows an embodiment of the optical system in a laser scanning eye fundus camera according to the present invention. The optical system of the eye fundus camera shown in FIG. 1 has an illuminating optical system for scanning the eye fundus $E_f$ of a subject's eye E with an illuminating laser beam, and a light receiving optical system for directing the reflected light from the eye fundus $E_f$ to a light receiver unit.

The illuminating optical system comprises a laser 1, a beam splitter 2, beam diameter adjusting means or spot diameter adjusting means in the form of a beam expander 3, a horizontal scanning member in the form of a polygonal mirror 4, variable power lenses 5 and 6, a vertical scanning member in the form of a galvanomirror 7, a relay lens 8, a focusing lens 9, and an objective lens 10. These elements are arranged in the order in which they are mentioned. In FIG. 1, P indicates a position which is conjugate with the pupil $E_p (P_0)$ of the subject's eye E, while R indicates another position which is conjugate with the eye fundus $E_f (R_o)$ of the subject's eye E.

In the illuminating optical system, the laser light beam generated by the laser 1 passes through the beam splitter 2 and then the diameter of the beam is varied by the beam expander 3. As shown, the beam expander 3 is removably placed in the optical path between the beam splitter 2 and the polygonal mirror 4. Further, the beam expander 3 is provided in a position which is conjugate with the pupil $E_p$ of the subject's eye E. The laser light beam having a diameter varied by the beam expander 3 impinges upon the polygonal mirror 4. The polygonal mirror 4 is driven by a motor (not shown) for rotation at a high speed, and reflects the laser beam from the beam expander 3 for scanning in a horizontal plane. The reflected laser beam passes through the variable power lenses 5, 6 and then falls onto the galvanomirror 7. The mirror 7 is rotataed through a predetermined angle in one direction thereby to deflect the laser beam in a vertical direction each time a horizontal scanning by the polygonal mirror 4 has been completed. The galvanomirror 7 is rotated back to the original position after a predetermined number of rotations, and therefore scannings for one frame, have been completed, and scannings for the next frame are initiated. The laser light reflected from the mirror 7 is projected onto the fundus $E_f$ of the subject's eye E through the relay lens 8, focus lens 9, and objective lens 10. Thus, the eye fundus $E_f$ of the subject's eye E is sequentially scanned with the laser light beam generated by the laser 1, which light beam produces a spot of constant diameter on the eye fundus. The operator can vary the spot diameter at will by replacing the beam expander 3 in the illuminating optical path with another beam expander.

The light receiving optical system shares most of its optical path with the illuminating optical system, and it uses the optical path extending between the objective lens and the beam splitter 2. The reflected light from the eye fundus $E_f$ of the subject's eye E passes through the light receiving optical system and reaches the light receiver unit in the form of a photomultiplier tube 11. The output signal from the photomultiplier tube 11 is picked up at intervals of the spot diameter by a microcomputer (not shown), and each of the thus picked up signals is stored in a memory (not shown) as a picture element. Thus, data corresponding to picture elements are sequentially stored in the memory and once the stored data is sufficient to construct one frame, the data of one-frame picture elements are sequentially transferred to a monitor CRT 12. An image of the eye fundus is thus constructed on the monitor CRT 12.

Figure 3:
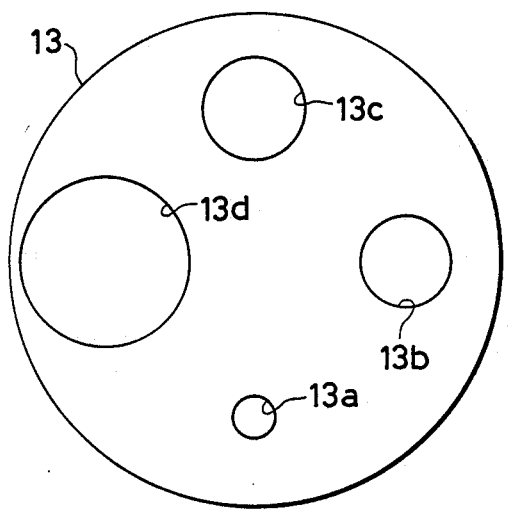
FIG. 3 is a plan view of an aperture plate which can be used in place of the beam expander shown in FIG. 1.

In the above-described embodiment, the beam expander 3 is interchangeable in its entirety with a substitute beam expander, but the present invention is not limited to such an arrangement. For example, an alternative example of the beam expander 3 shown in FIG. 2 comprises two lens elements $L_1$ and $L_2$, of which the latter element $L_2$ can be selected from a set of alternative lenses which have different focal lengths and which can be removably placed in the optical path. In this example, the beam diameter can be changed by selectively placing one of said alternative lenses. Another substitute for the beam expander 3 is shown in FIG. 3, which comprises an aperture plate 13 having a plurality of apertures 13a, 13b, 13c, 13d of different diameters which can be selectively positioned in the optical path. Further, the beam expander 3 may be replaced by a zoom optical system which allows to change the beam diameter continuously.

Meanwhile, when observation is performed at a high magnification using a variable power device capable of up to a considerably high magnification, the image may sometimes be indistinct partially, since eye fundi are not smooth but rugged.

For such a purpose, therefore, the spot diameter adjusting means should be arranged such that it allows the operator to vary the beam diameter at will and, when the magnification for observation is changed, the spot diameter is automatically varied by an amount which corresponds in some manner to the change in magnification.

Using the so arranged spot diameter adjusting means, the spot diameter is enlarged and the depth of focus is increased when the magnification is increased, so that all the portions of the image within the observed region can be sharply focused.

When the subject is very young, for example, and tends to move the eyes during the observation, the above-described embodiments allow the operator to enlarge the spot diameter thereby to obtain a clear image of the eye fundus in spite of slight movement of the subject's eye. Further, the spot diameter can be reduced to obtain a higher resolution.

Figure 6:
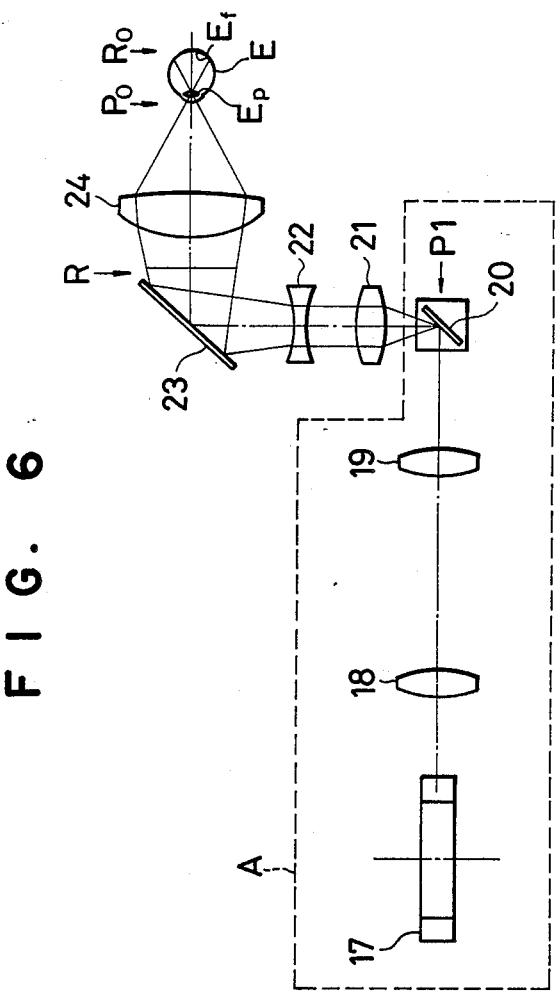
FIG. 6 is a side view showing the arrangement of a portion of the optical system shown in FIG. 5.
Figure 7:
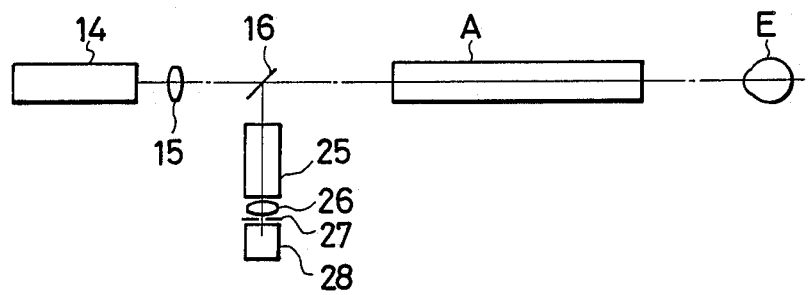
FIG. 7 is a schematic illustration showing the optical system of FIGS. 5 and 6.

FIGS. 5-7 show another embodiment of the present invention.

The optical system in the eye fundus camera shown in FIGS. 5-7 comprises an illuminating optical system for scanning the eye fundus $E_f$ with an illuminating laser light beam, and a light receiving optical system for directing the reflected light from the eye fundus $E_f$ to a light receiver unit.

The illuminating optical system in this embodiment includes a light source in the form of a laser 14, a lens 15, a beam splitter 16, a horizontal scanning member in the form of a polygonal mirror 17, variable power lenses 18 and 19, a vertical scanning member in the form of a galvanomirror 20, a relay lens 21, a focusing lens 22, a reflecting mirror 23 and an objective lens 24. These elements are arranged in the order in which they are mentioned. The elements from the polygonal mirror 17 to the galvanomirror 20 form in combination an optical scanning device A. In the figures, P indicates a position which is conjugate with the pupil $E_p$ ($P_o$) of the subject's eye E, while R indicates a position which is conjugate with the fundus $E_f$ ($R_o$) of the subject's eye E.

The laser beam from the laser 14 of the illuminating optical system passes through the lens 15 and through the beam splitter 16, and then impinges upon the polygonal mirror 17. The polygonal mirror 17, while rotating at a high speed, deflects the incident laser beam for scanning in a horizontal plane. The so deflected laser beam is guided through the variable power lenses 18 and 19, the galvanomirror 20, the relay lens 21, the focusing lens 22 and the reflecting mirror 23, and is then projected onto the fundus $E_f$ of the subject's eye E. Then, the galvanomirror 20 is rotated through a predetermined angle each time a horizontal scanning by the polygonal mirror 17 is completed, whereby the horizontal line to be scanned with the laser light is vertically shifted. Such scanning will form a scanned surface in the fundus $E_f$ of the subject's eye E.

The light receiving optical system comprises the above-mentioned optical system from the beam splitter 16 to the objective lens 24, beam diameter adjusting means in the form of a beam expander 25, a condenser lens 26, a pinhole plate 27 and a light receiver unit in the form of a photodiode 28. The reflected light beam from the eye fundus $E_f$ is guided through the objective lens 24, the reflecting mirror 23, the focusing lens 22, the relay lens 21, the galvanomirror 20, the variable power lenses 14 and 18 and the polygonal mirror 17 and then impinges upon the beam splitter 16 which in turn reflects the incident light beam toward the beam expander 25. The reflected light beam passes through the beam expander 25, whereby the beam diameter is adjusted, and it is then converged at a pin-hole 27a in the pin-hole plate 27 by means of the condenser lens 26 and then enters the photodiode 28.

When there is no shading or eclipse in the scanning device A or the lenses, the diameter of the aperture of the light receiving optical system for receiving the reflected light beam is defined by the effective aperture of the beam expander 25. It is therefore possible to vary the aperture diameter by selectively placing in the optical path one of a set of beam expanders 25 having different magnifications.

Assuming that the magnification at which the pinhole 27a in the pin-hole plate 27, which is situated immediately before the photodiode 28, is geometrically projected onto the eye fundus $E_f$ by the light receiving optical system, is "magnification of projection", the resolution will be changed as follows, by adjusting the beam expander 25: by increasing the aperture diameter of the light receiving optical system by means of the beam expander 25, the magnification of projection is reduced with the result that the resolution is increased but the depth of field is reduced; conversely, by decreasing the aperture diameter by means of the beam expander 25, the magnification of projection is increased with the result that the resolution is decreased but the depth of field is increased.

Such nature allows the operator to adjust the aperture diameter in view of the subject or of the selected magnification of observation, so as to observe the subject's eye E in the most convenient manner. Since the change in the aperture diameter will produce a change in the quantity of the received light, it is desirable to provide, in the optical system, means for automatically adjusting the intensity of illumination in an interconnected manner.

FIG. 7 schematically shows the optical system shown in FIGS. 5 and 6. The optical scanning device A includes the optical elements from the polygonal mirror 17 to the galvanomirror 20, as stated above. In FIG. 7, the optical elements from the above-mentioned relay lens 21 to the objective lens 24 are not shown.

Figure 8:
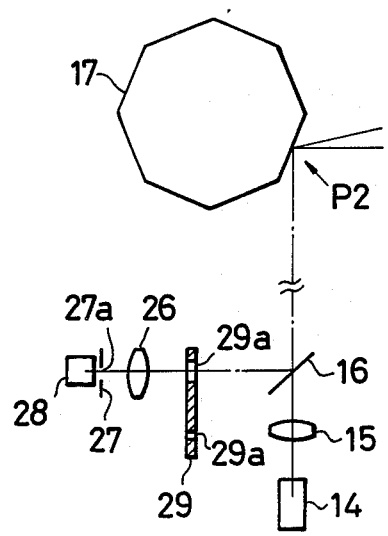
FIG. 8 is an illustration showing an alternative example of the light beam diameter adjusting means shown in FIG. 5.

The embodiments described above include a beam expander 25 as the beam diameter adjusting means. The invention is however not limited to such an arrangement. For example, FIG. 8 shows an alternative beam diameter adjusting means which comprises an aperture plate 29 placed between the beam splitter 16 and the condenser lens 26. The plate 29 is provided with a plurality of circumferentially disposed apertures 29a which have different diameter.

FIGS. 9 through 12 show various arrangements of the beam expander 25 as the beam diameter adjusting means in an eye fundus camera having a single optical scanning device A provided in the common optical path of the illuminating optical system and of the light receiving optical system. In these figures, the optical elements from the relay lens 21 to the objective lens are again not shown.

Figure 9:
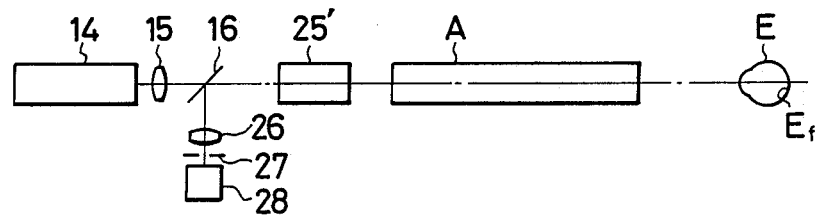
FIGS. 9-15 are schmatic illustrations showing further embodiments of the optical system in the laser scanning eye fundus camera according to the present invention.

FIG. 9 shows an embodiment which lacks the beam expander 25 shown in FIG. 5 between the beam splitter 16 and the condenser lens 26, while having a beam expander 25' placed between the beam splitter 16 and the optical scanning device A. In this embodiment, the only beam expander 25 allows the operator to simultaneously adjust both of the diameter of the laser light spot projected onto the eye fundus $E_f$ from the laser 14, and the diameter of the reflected light beam from the eye fundus $E_f$.

Figure 10:
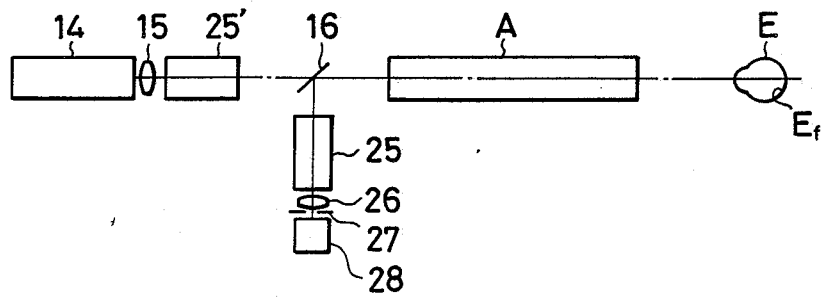

FIG. 10 shows another embodiment having first beam diameter adjusting means in the form of a first beam expander 25' provided between the beam splitter 16 and the system of the lens 15 and the laser 14, and second beam diameter adjusting means in the form of a second beam expander 25 provided between the beam splitter 16 and the condenser lens 26. The present embodiment allows the operator to separately adjust the diameter of the laser light spot projected onto the fundus $E_f$ from the laser 14 and the diameter of reflected light beam from the eye fundus $E_f$.

Figure 11:
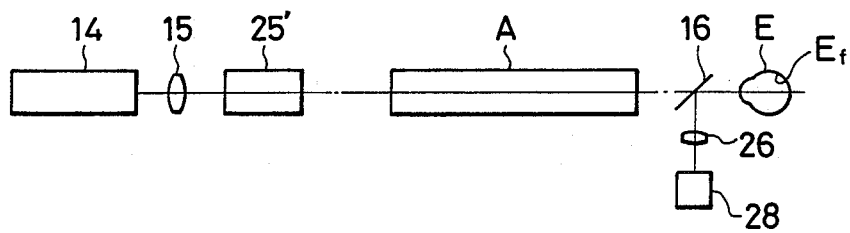

FIG. 11 shows another embodiment which is similar to the embodiment shown in FIG. 9, but in which the beam splitter assembly of the optical system comprising the beam splitter 16, the condenser lens 26 and the photodiode 28 is positioned between the optical scanning device A and the subject's eye E. Here, the reflecting mirror 23 shown in FIG. 5 can be replaced by the beam splitter 16.

Figure 12:
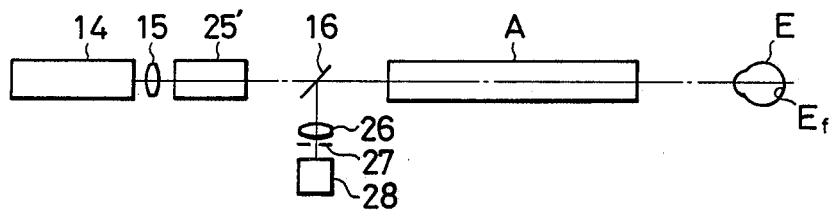

FIG. 12 shows a further embodiment which is similar to that shown in FIG. 10 but which lacks the beam expander 25 between the beam splitter 16 and the condenser lens 26.

Figure 13:
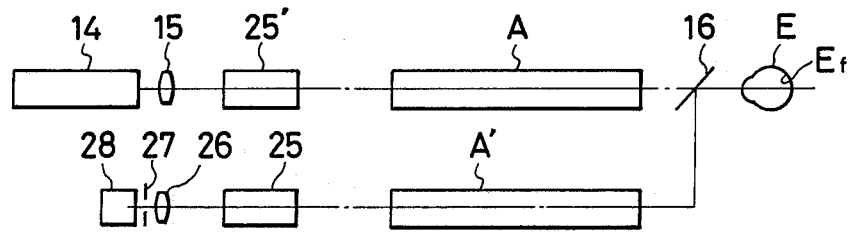
Figure 14:
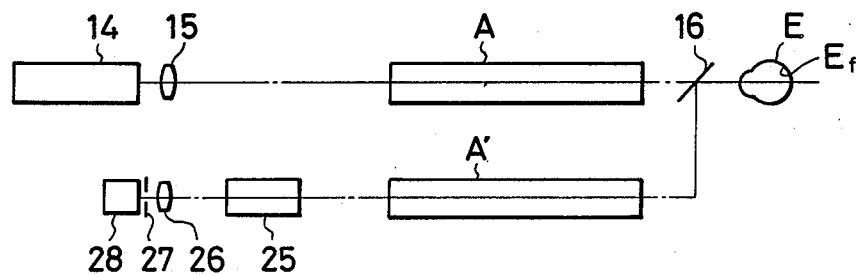
Figure 15:
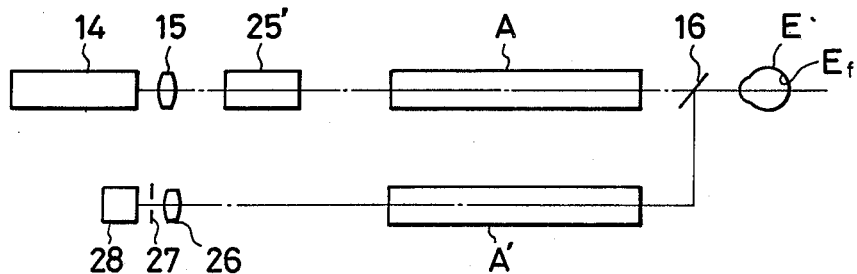

FIGS. 13-15 show various arrangements of the beam expander 25 in an eye fundus camera which has the beam splitter 16 placed between the relay lens 21 (also shown in FIGS. 5 and 6) and the subject's eye E, a first optical scanning device A provided between the beam splitter 16 and the system of the lens 15 and the laser 14, and a second optical scanning device A' provided between the beam splitter 16 and the condenser lens 26. The optical elements from the above-mentioned relay lens 21 to the objective lens 24 of these embodiments are not shown in FIGS. 13-15.

The embodiment shown in FIG. 13 includes a first beam diameter adjusting means in the form of a first beam expander 25' provided between the optical scanning device A and the system of the lens 15 and the laser 14, and a second beam diameter adjusting means in the form of a second beam expander 25 provided between another optical scanning device A' and the condenser lens 26.

The embodiment shown in FIG. 14 is similar to that of FIG. 13 but lacks the first beam expander 25'.

The embodiment shown in FIG. 15 is similar to that of FIG. 13 but lacks the second beam expander 25.

As described above, the optical system in a laser scanning eye fundus camera according to the invention comprises: an illuminating optical system for scanning the eye fundus with a laser beam from a light source using an optical scanning device; and a light receiving optical system for directing the reflected light from the eye fundus through the optical scanning device to a light receiver unit. The optical system according to the invention further includes beam diameter adjusting means for adjusting the diameter of said laser light beam. Such arrangement according to the present invention allows to adjust the depth of field by adjusting the aperture diameter of the optical system by means of the beam diameter adjusting means so that test or inspection of even or uniform quality can be ensured for all subjects in spite of variations in their age, experience of medical or ophthalmological tests or inspections, or structure of the eye fundus.

Further, when beam diameter adjusting means for adjusting the diameter of the reflected laser light beam from the eye fundus is provided at least in said light receiving optical system, the aperture diameter of the light receiving optical system can be adjusted in view of the subject's age, experience of test or inspection, or the structure of the eye fundus, so that the depth of field can be easily adjusted to suitably adjust the resolution or to bring into focus the overall eye fundus being rugged.

What is claimed is:

1. An optical system in a laser scanning eye fundus camera comprising:
   an illuminating optical system for illuminating an eye fundus through an eye pupil by scanning the eye fundus with an illuminating laser light from a laser light source by means of an optical scanning device;
   a light receiving optical system for conducting the reflected light reflected from the eye fundus to a light receiver unit, in which said light receiving optical system and said illuminating optical system have a common optical scanning device, said light receiving optical system including a display device for displaying an image of the eye fundus in response to a signal from said light receiver unit, said display device including magnification adjusting means for changing the magnification of the image of the eye fundus on said display device; and
   beam diameter adjusting means provided in said illuminating optical system conjugate with the intended position of the pupil for adjusting the beam diameter of the laser beam projected onto said eye fundus, in which said beam diameter adjusting means is placed between the laser light source and the optical scanning device, in which the reflected light from the eye fundus is directed to the light receiver unit through a beam splitter placed between said beam diameter adjusting means and said optical scanning device, and in which second beam diameter adjusting means, separate from said beam diameter adjusting means, is provided between the beam splitter and the light receiver unit, whereby an operator may separately adjust the diameter of the laser light projected onto the eye fundus and the diameter of the reflected light beam from the eye fundus.

* * * * *